United States Patent
Zhong (10) Patent No.: US 8,032,321 B2
(45) Date of Patent: Oct. 4, 2011

(54) MULTI-LAYERED BIOSENSOR ENCODING SYSTEMS

(75) Inventor: Weiping Zhong, Granger, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 0 days.

(21) Appl. No.: 12/173,139

(22) Filed: Jul. 15, 2008

(65) Prior Publication Data
US 2010/0017165 A1   Jan. 21, 2010

(51) Int. Cl.
*G01D 18/00* (2006.01)

(52) U.S. Cl. .............. 702/104; 702/19; 702/20; 702/21; 702/22; 702/23; 702/24; 702/25; 702/26; 702/27; 702/28; 702/29; 702/30; 702/31; 702/32; 702/168

(58) Field of Classification Search .............. 702/19–32, 702/104, 168
See application file for complete search history.

(56) References Cited

U.S. PATENT DOCUMENTS

| | | | |
|---|---|---|---|
| 4,714,874 A | 12/1987 | Morris et al. | |
| 5,281,395 A | 1/1994 | Markart et al. | |
| 5,445,967 A | 8/1995 | Deuter | |
| 5,510,266 A | 4/1996 | Bonner et al. | |
| 5,575,403 A | 11/1996 | Charlton et al. | |
| 5,856,195 A | 1/1999 | Charlton et al. | |
| 5,863,800 A | 1/1999 | Eikmeier et al. | |
| 6,599,406 B1 | 7/2003 | Kawanaka et al. | |
| 6,814,844 B2 | 11/2004 | Bhullar et al. | |
| 2003/0013941 A1 | 1/2003 | Cohn et al. | |
| 2004/0019653 A1 | 1/2004 | Debaty et al. | |
| 2004/0019686 A1 | 1/2004 | Toyoda et al. | |
| 2004/0156832 A1 | 8/2004 | Jolly | |
| 2004/0200721 A1 | 10/2004 | Bhullar et al. | |
| 2004/0244151 A1 | 12/2004 | Sakata et al. | |
| 2005/0016845 A1 | 1/2005 | Groll et al. | |
| 2005/0016846 A1 | 1/2005 | Groll et al. | |
| 2005/0019805 A1 | 1/2005 | Groll | |
| 2005/0019945 A1 | 1/2005 | Groll et al. | |
| 2005/0019953 A1 | 1/2005 | Groll et al. | |
| 2005/0023137 A1* | 2/2005 | Bhullar et al. | 204/403.1 |
| 2005/0076845 A1 | 4/2005 | Langdale | |
| 2005/0079945 A1 | 4/2005 | Wittkopp | |
| 2005/0161345 A1 | 7/2005 | Groll et al. | |
| 2005/0226846 A1 | 10/2005 | Umlauf et al. | |
| 2005/0279647 A1 | 12/2005 | Beaty et al. | |
| 2006/0189895 A1 | 8/2006 | Neel et al. | |
| 2009/0030617 A1* | 1/2009 | Schell et al. | 702/19 |
| 2009/0125268 A1* | 5/2009 | Perry | 702/100 |

FOREIGN PATENT DOCUMENTS

| | | |
|---|---|---|
| EP | 1152239 | 11/2001 |
| EP | 1475630 | 11/2004 |
| WO | WO 2004113914 | 12/2004 |
| WO | WO 2004113915 | 12/2004 |
| WO | WO 2005001474 | 1/2005 |
| WO | WO 2006035322 | 4/2006 |
| WO | WO 2006113723 | 10/2006 |
| WO | WO 2006113865 | 10/2006 |

* cited by examiner

*Primary Examiner* — Sujoy Kundu
(74) *Attorney, Agent, or Firm* — Nixon Peabody LLP (57) ABSTRACT

A biosensor system determines the presence and/or concentration of an analyte in a sample using one or more calibrated correlation equations. The analysis may be electrochemical, optical, or a combination thereof. The biosensor system may be implemented using a measurement device and a sensor strip. The measurement device applies test signals to a multi-layered encoding area of the sensor strip. Calibration information is determined from the patterns generated by the interaction of the test signals with the multi-layered encoding area.

26 Claims, 8 Drawing Sheets

MULTI-LAYERED BIOSENSOR ENCODING SYSTEMS

BACKGROUND

Biosensors provide an analysis of a biological fluid, such as whole blood, serum, plasma, urine, saliva, interstitial, or intracellular fluid. Typically, biosensors have a measurement device that analyzes a sample residing in a sensor strip. The sample is typically in liquid form and in addition to being a biological fluid, may be the derivative of a biological fluid, such as an extract, a dilution, a filtrate, or a reconstituted precipitate. The analysis performed by the biosensor determines the presence and/or concentration of one or more analytes, such as alcohol, glucose, uric acid, lactate, cholesterol, bilirubin, free fatty acids, triglycerides, proteins, ketones, phenylalanine or enzymes, in the biological fluid. The analysis may be useful in the diagnosis and treatment of physiological abnormalities. For example, a diabetic individual may use a biosensor to determine the glucose level in whole blood for adjustments to diet and/or medication.

Biosensors may be designed to analyze one or more analytes and may use different sample volumes. Some biosensors may analyze a single drop of whole blood, such as from 0.25-15 microliters (µL) in volume. Biosensors may be implemented using bench-top, portable, and like measurement devices. Portable measurement devices may be handheld and allow for the identification and/or quantification of one or more analytes in a sample. Examples of portable measurement devices include the Ascensia Breeze® and Elite® meters of Bayer HealthCare in Tarrytown, N.Y., while examples of bench-top measurement devices include the Electrochemical Workstation available from CH Instruments in Austin, Tex. Biosensors providing shorter analysis times, while supplying the desired accuracy and/or precision, provide a substantial benefit to the user.

Biosensors may be adapted for use outside, in contact with, inside, or partially inside a living organism. When used outside a living organism, a sample of the biological fluid is introduced into a sample reservoir in the sensor strip. The sensor strip may be placed in the measurement device before, after, or during the introduction of the sample for analysis. When in contact with the living organism, the sensor strip may be attached to the skin where fluid communication is established between the organism and the strip. When inside or partially inside a living organism, the sensor strip may be continually immersed in the fluid or the fluid may be intermittently introduced to the strip for analysis. The sensor strip may include a reservoir that partially isolates a volume of the fluid or be open to the fluid. When in contact with, partially inside, or inside a living organism, the measurement device may be connected to the sensor strip with wires or wirelessly, such as by RF, light-based, magnetic, or other communication techniques.

Biosensors may use optical and/or electrochemical methods to analyze the sample. In some optical systems, the analyte concentration is determined by measuring light that has interacted with a light-identifiable species, such as the analyte or a reaction or product formed from a chemical indicator reacting with the analyte redox reaction. In other optical systems, a chemical indicator fluoresces or emits light in response to the analyte redox reaction when illuminated by an excitation beam. In either optical system, the biosensor measures and correlates the light with the analyte concentration of the biological sample.

In electrochemical methods, the analyte concentration is determined from an electrical signal generated by an oxidation/reduction or redox reaction of the analyte when an input signal is applied to the sample. The electrical signal may be a current (as generated by amperometry), a potential (as generated by voltammetry or potentiometry), or an accumulated charge (as generated by coulometry). An enzyme or similar species may be added to the sample to enhance the redox reaction. The input signal may be a current or potential. In electrochemical methods, the biosensor measures and correlates the electrical signal with the concentration of the analyte in the biological fluid.

In electrochemical biosensors, the measurement device usually has electrical contacts that connect with electrical conductors in the sensor strip. The conductors are formed from an electrically conductive material, such as solid metals, metal pastes, conductive carbon, conductive carbon pastes, conductive polymers, and the like. The electrical conductors typically connect to working, counter, and/or other electrodes that extend into a sample reservoir. The measurement device applies the input signal through the electrical contacts to the electrical conductors of the sensor strip. The electrical conductors convey the input signal through the electrodes into the sample present in the sample reservoir. The redox reaction of the analyte generates an electrical signal in response to the input signal. The measurement device determines the analyte concentration in response to the electrical signal.

Sensor strips may have an encoding area that provides coding information to the measurement device. The measurement device may use the coding information to adjust the analysis of the biological fluid in response to one or more parameters, such as the identification information indicating the type of sensor strip, the type of biological fluid, the particular analyte(s), the manufacturing lot of the sensor strip, and the like. The encoding area may be a separate component or may be partially or fully integrated with other components on the sensor strip. The coding information may indicate the correlation equation to use, changes to the correlation equation, or the like.

Correlation equations are mathematical representations of the relationship between the electrical signal and the analyte in an electrochemical biosensor or between light and the analyte in an optical biosensor. Correlation equations may be implemented to manipulate the electrical signal or light for determination of the analyte concentration. Correlation equations also may be implemented as a program number assignment (PNA) table of slopes and intercepts for the correlation equations, another look-up table, or the like. The measurement device uses the coding information to adjust the analysis of the biological fluid.

Coding information may be obtained from the encoding area either electrically or optically. Some encoding areas may be read only electrically or only optically. Other encoding areas may be read electrically and optically. Electrical encoding areas usually have one or more electrical circuits with multiple contacts or pads. The measurement device may have one or more conductors that connect with each contact on the encoding area of the sensor strip. Typically, the measurement device applies an electrical signal through one or more of the conductors to one or more of the contacts on the encoding area. The measurement device measures the output signal from one or more of the contacts. The measurement device may determine the coding information from the absence or presence of output signals from the contacts on the encoding area. The measurement device may determine the coding information from the electrical resistance of the output signals from the contacts on the encoding area.

In some electrical encoding areas, the measurement device determines the coding information from the absence or presence of different contacts. If the measurement device measures an output signal from the location of a contact, then the measurement device presumes a contact is present. If the measurement device does not measure an output signal, then the measurement device presumes a contact is absent.

In other electrical encoding areas, the measurement device determines the coding information from the resistance of the electrical output signal from the contact. Typically, the amount of conductive material associated with each contact varies, thus changing the electrical resistance. The length and thickness of the connection between the contacts and the electrical circuit also may be varied to alter the resistance.

Accordingly, there is an ongoing need for improved biosensors, especially those that may provide increasingly accurate and/or precise analyte concentration measurements. The systems, devices, and methods of the present invention overcome at least one of the disadvantages associated with encoding areas used in biosensors.

SUMMARY

The present invention provides a biosensor system that calibrates an analyte analysis to determine an analyte concentration in a biological fluid. The biosensor system senses patterns on a sensor strip. The patterns provide calibration information, which the biosensor system may use to calibrate one or more correlation equations used in the analyte analysis. The analyte concentration is determined using one or more calibrated correlation equations.

A biosensor may have a measurement device and a sensor strip. The measurement device may have a processor connected to a pattern read device. The sensor strip has a multi-layered encoding area with two or more patterns. The patterns may be electrical connectivity, the ability to alter a light beam, or a combination thereof. The measurement device and the sensor strip may implement an analyte analysis. The analyte analysis may have one or more correlation equations. The pattern read device may sense at least two patterns on the multi-layered encoding area of the sensor strip. The processor may determine calibration information in response to the patterns. The processor may calibrate at least one correlation equation in response to the calibration information. The processor may determine an analyte concentration in response to one or more calibrated correlation equations.

Another biosensor may have a measurement device and a sensor strip. The measurement device may have a processor connected to a pattern read device. The pattern read device may have an array of electrical contacts. The sensor strip may have a multi-layered encoding area with at least a first layer and a second layer. The encoding area has at least two electrical connectivities, where at least one connectivity has at least one contact area on the first layer and at least one contact area on the second area. The contact areas may be in electrical communication with the electrical contacts. The measurement device and sensor strip may implement an analyte analysis. The analyte analysis may have one or more correlation equations. The electrical contacts may selectively apply test signals to the contact areas on the multi-layered encoding area. The pattern read device may sense at least two patterns on the multi-layered encoding area. The processor may determine calibration information in response to the patterns. The processor may calibrate one or more correlation equations in response to the calibration information. The processor may determine an analyte concentration in response to one or more calibrated correlation equations.

In a method for calibrating an analysis of an analyte in a biological fluid, at least two patterns on a multi-layered encoding area are sensed. The patterns may be electrical connectivity, the ability to alter a light beam, or a combination thereof. Calibration information is determined in response to the patterns. One or more correlation equations are calibrated in response to the calibration information. An analyte concentration is determined in response to one or more calibrated correlation equations.

BRIEF DESCRIPTION OF THE DRAWINGS

The invention may be better understood with reference to the following drawings and description. The components in the figures are not necessarily to scale, emphasis instead being placed upon illustrating the principles of the invention.

DETAILED DESCRIPTION

A biosensor system uses coding information to analyze a sample. The biosensor system has a measurement device that applies test signals to a multi-layered encoding area. The measurement device senses differences between at least a first layer and a second layer in response to the test signals. For electrical devices, the differences arise from varying circuit patterns, while for optical devices; the differences arise from alteration of at least one light beam by at least two layers.

For electrical devices, the circuit patterns may be sensed by determining electrical connectivity or the degree of electrical connectivity between at least two contact areas of the multi-layered encoding area. Each layer may have two or more contact areas, while each contact area may be in electrical communication with one or more contact. For optical devices, the varying interactions of the at least one light beam with the at least two layers may be determined from an alteration in color, refractive index, fluorescence, absorption, transmission, reflection, refraction, scattering, combinations thereof, and the like.

The circuit patterns or optical alterations provide calibration information, which the biosensor system uses to calibrate an optical and/or electrochemical analysis. The measurement device may use the calibration information to calibrate one or more correlation equations used in the analysis. The measurement device determines the analyte concentration using one or more of the calibrated correlation equations.

Figures 1A, 1B, 1C:
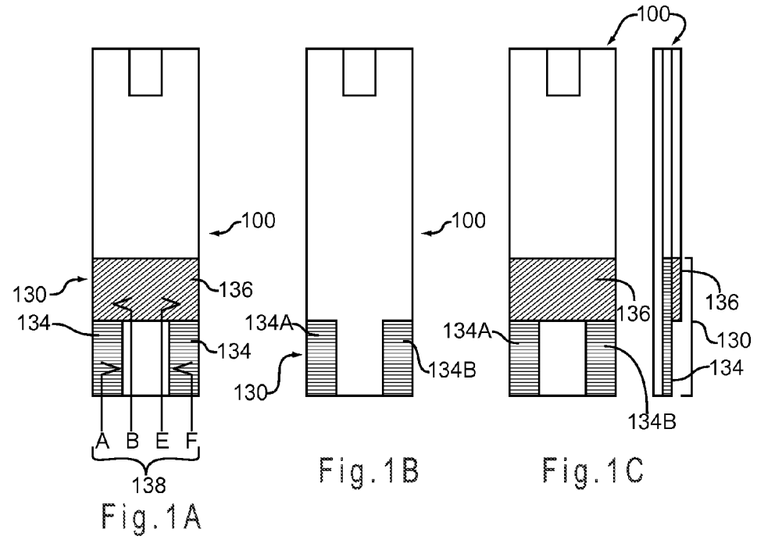
FIG. 1A depicts a sensor strip having a multi-layered encoding area, where an array of electrical contacts is in electrical communication with the encoding area.
FIG. 1B depicts a sensor strip having an encoding area where a first conductive area is divided into two electrically-isolated portions.
FIG. 1C depicts a sensor strip having a multi-layered encoding area, where a second conductive area is disposed on the first conductive area.

FIG. 1A represents a sensor strip 100 having a multi-layered encoding area 130, where an array of electrical contacts 138 (A, B, E, and F) are in electrical communication with the encoding area 130. Electrical contacts A and F are in electrical communication with a first conductive area 134, while electrical contacts B and E are in electrical communication with a second conductive area 136. As represented in FIG. 1B, the first conductive area 134 may be divided into two or more electrically-isolated portions, such as 134A and 134B. As represented in FIG. 1C, the multi-layered encoding area 130 is formed by disposing the second conductive area 136 on the first area 134, where the second area 136 is substantially electrically isolated from the first area 134. The conductive material forming the conductive areas may have a rectangular or square shape, and may have other shapes such as triangular, circular, elliptical, a combination of shapes, or the like.

Figure 1D:
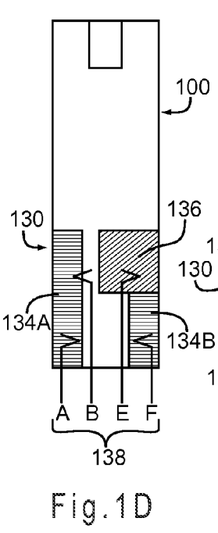
FIGS. 1D and 1E depict sensor strips having multi-layered encoding areas, where a portion of the second conductive area is removed from a portion of the first area.
Figures 1E, 1F, 1G:
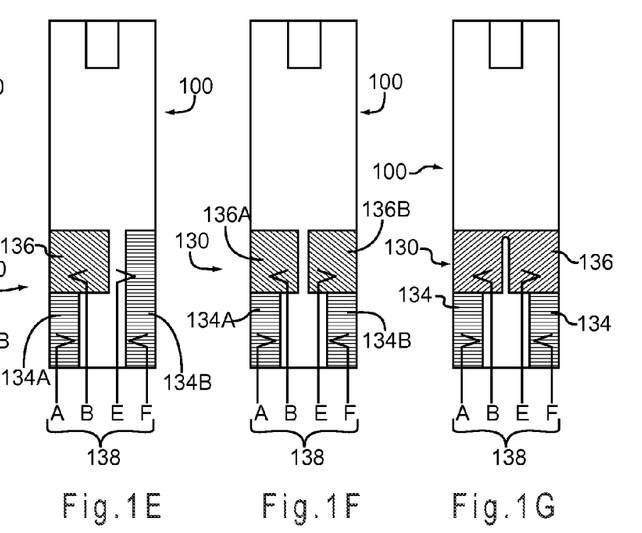
FIG. 1F depicts a sensor strip having a multi-layered encoding area, where the second conductive area is divided between the electrically-isolated portions of the first conductive area.
FIG. 1G depicts a sensor strip having a multi-layered encoding area, where the second area is partially divided to provide a change in resistance.

FIGS. 1D and 1E depict the encoding area 130 having a portion of the second area 136 removed from the first conductive area 134A or the first conductive area 134B, respectively. By selectively removing a portion of the second conductive area 136 from the first conductive area 134, an electrical contact that contacted the second area 136 now may contact the conductive area 134. Thus, for FIG. 1D electrical contact B no longer contacts the second area 136, but now contacts the first conductive area 134A. Similarly, for FIG. 1E electrical contact E no longer contacts the second area 136, but now contacts the first conductive area 134B. While particular configurations are shown, the sensor strip 100, the encoding area 130, and the array 138 may have other configurations including those with additional components.

FIG. 1F represents the encoding area 130 where the second area 136 is divided between the electrically-isolated portions of the first conductive area 134 to provide second conductive areas 136A and 136B. In this manner, electrical connectivity is substantially broken between electrical contacts B and E, providing each of the contacts with an electrically isolated contact area. FIG. 1G represents a variation on FIG. 1F where the second area 136 is partially divided between electrical contacts B and E, thus providing a change in the degree of electrical connectivity (resistance) between the contacts. While particular configurations are shown, the sensor strip 100, the encoding area 130, and the array 138 may have other configurations, including those with additional components.

The array of electrical contacts 138 may be part of a pattern read device that uses the electrical contacts to sense the circuit patterns of the encoding area 130. The pattern read device may apply test signals to the circuits 134 and 136 through the array of electrical contacts 138 in response to a control signal.

The test signals may be electrical signals such as current, potential, or the like. The current may be selected to provide short-circuit protection and/or to accommodate the resistance of the material used to produce the circuit patterns. The test signals may be limited to a current of less than about 50 microAmperes (µA). The test signals may be current limited in the range of about 1 µA through about 48 µA, in the range of about 2 µA through about 15 µA, in the range of about 2 µA through about 10 µA, or in the range of about 4 µA through about 8 µA. Other currents or potentials may be used.

A pattern read device selectively applies the test signals to sense the circuit patterns from the electrical connectivity and/or the degree of electrical connectivity between the contacts 138. Table I, below, depicts the electrical connectivity of the electrical contacts 138 for FIGS. 1A and 1D-1F, which establish at least five different states of electrical connectivity. The pattern read device may provide a digital or analog representation of the varying connectivity to a processor in a measurement device. The processor may convert the digital or analog representation into the calibration information. For example, a connection may be interpreted as "1", while a lack of connection may be interpreted as "0". Other number assignments may be used and may result in different digital representations.

TABLE I

| FIG. No. | B-E Connected | B-A Connected | E-F Connected |
|---|---|---|---|
| 1B | No (0) | Yes (1) | Yes (1) |
| 1C | Yes (1) | No (0) | No (0) |
| 1D | No (0) | Yes (1) | No (0) |
| 1E | No (0) | No (0) | Yes (1) |
| 1F | No (0) | No (0) | No (0) |

In addition to electrical connectivity, the degree of electrical connectivity may be used to provide calibration information. The degree of electrical connectivity between any two or more contacts may be selected by using materials of different resistance or area because the resistance through a conductive material is responsive to the resistance and area of the material electrically traversed. For example, if the material of the second conductive area 136 of FIG. 1A has a higher resistance than the material of the first conductive area 134 and the first and second layers are not electrically isolated, the resistance between contacts B and E will be larger than between contacts A and B. In this manner, the degree of electrical connectivity between B-E versus A-B allows the contacts to be distinguished. Additional methods also may be used to alter the degree of electrical connectivity, such as placing an additional conductive material between the layers and the like.

The degree of electrical connectivity between the contacts B and E also may be selected by partially severing the conductive material between the contacts. For example, FIG. 1G depicts a variation of the multi-layered encoding area 130 of FIG. 1A where the second conductive area 136 has been partially severed. As shown in the figure, the electrical connectivity between contacts B and E is reduced in one portion of the second conductive area 136 to the distance of d2−d1, and the resistance between contacts B and E may be proportional to 1/(d2−d1). Thus, the degree of electrical connectivity between the contacts may be selected by altering the conductivity of the material or materials used to form the encoding area 230 or by altering the area of the material or materials present between the contacts.

Figure 2A:
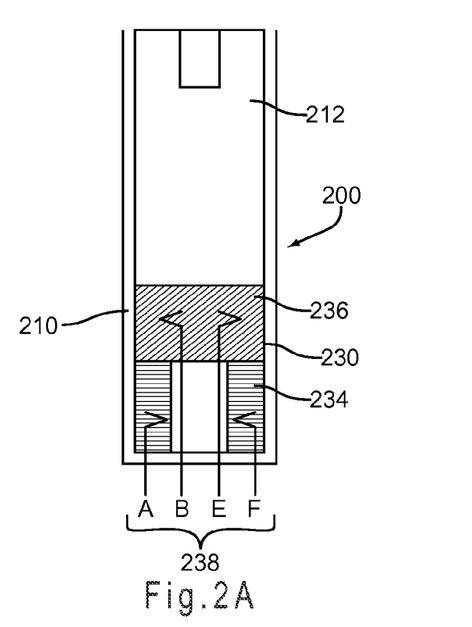
FIG. 2A represents another sensor strip including a substrate having a multi-layered encoding area, where an array of electrical contacts is in electrical communication with the encoding area.

FIG. 2A represents a sensor strip 200 including a substrate 210 and a cover 212, where an array of electrical contacts 238 (A, B, E, and F) is in electrical communication with a multi-layered encoding area 230. The multi-layered encoding area 230 includes a first conductive layer 234 disposed on the substrate 210, and at least one second conductive layer 236. The first conductive layer 234 may serve as the substrate 210. An insulating layer 215 may reside between the first and second conductive layers 234, 236. The second conductive layer 236 may serve as the cover 212 of the sensor strip 200. While not shown in the figure, the first conductive layer 234 may be cut between contact areas B and E to electrically isolate the contacts as previously described.

Figure 2B:
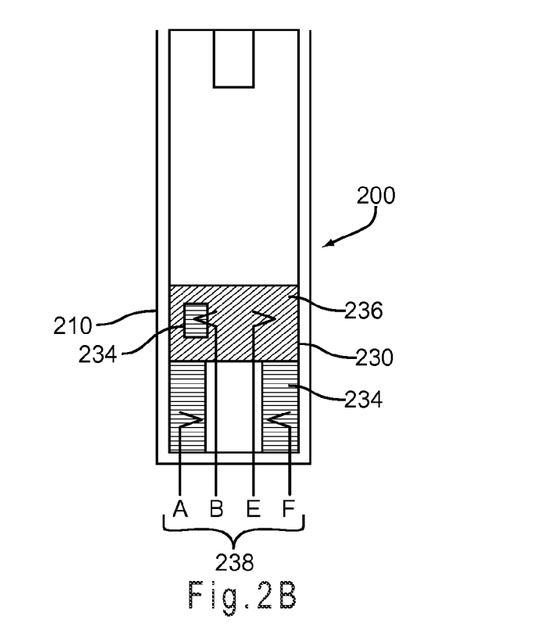
FIGS. 2B-2D represents the sensor strip of FIG. 2A where one or more portions of the second conductive layer is removed.
Figure 2C:
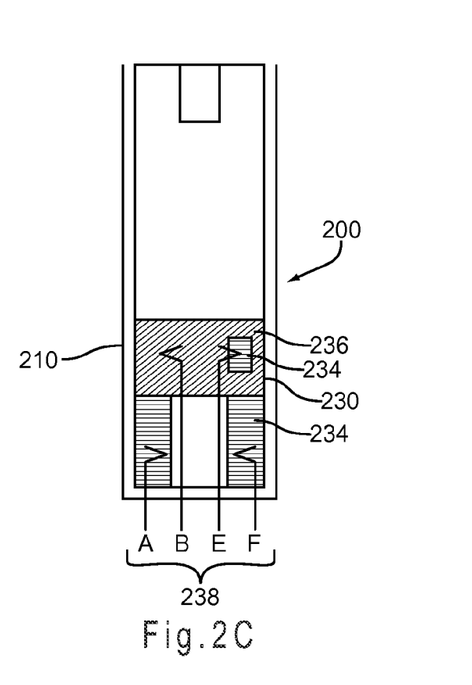
Figure 2D:
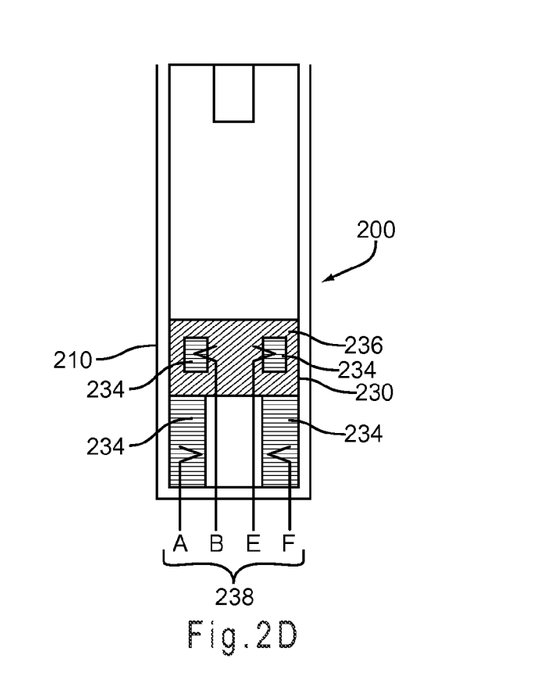

FIG. 2B represents the sensor strip 200 where a portion of the second conductive layer 236 is removed under contact B to provide electrical communication between contacts A and B, while contacts E and F remain electrically isolated. Similarly, FIG. 2C represents the sensor strip 200 where a portion of the second conductive layer 236 may be removed under contact E to provide electrical communication between contacts E and F, while contacts A and B remain electrically isolated. In FIG. 2D, removing a portion of the second conductive layer 236 under contacts B and E provides electrical communication between contacts A and B and between E and F. While the second conductive layer is depicted as being removed in rectangular areas, any size or shape of material may be removed that is consistent with the operation of the biosensor. Any method compatible with the production and use of the sensor strip 200 may be used to remove the material, such as laser ablation, scribing, photo etching, or like technique. In contrast to removal techniques, the second conductive layer 236 also may be selectively deposited to exclude areas under the desired contact or contacts.

Table II, below, depicts the electrical connectivity of the electrical contacts 238 for FIGS. 2A-2D, which establish at least 4 different states of electrical connectivity. The pattern read device may provide a digital or analog representation of the varying connectivity to a processor. The processor may convert the digital or analog representation into the calibration information. For example, a connection may be interpreted as "1", while a lack of connection may be interpreted as "0". Other number assignments may be used and may result in different digital representations.

TABLE II

| FIG. No. | A-B Connected | E-F Connected | B-E Connected | B-F Connected | E-A Connected |
|---|---|---|---|---|---|
| 2A | No (0) | No (0) | Yes (1) | No (0) | No (0) |
| 2B | Yes (1) | No (0) | No (0) | No (0) | No (0) |
| 2C | No (0) | Yes (1) | No (0) | No (0) | No (0) |
| 2D | Yes (1) | Yes (1) | No (0) | No (0) | No (0) |

Figure 3A:
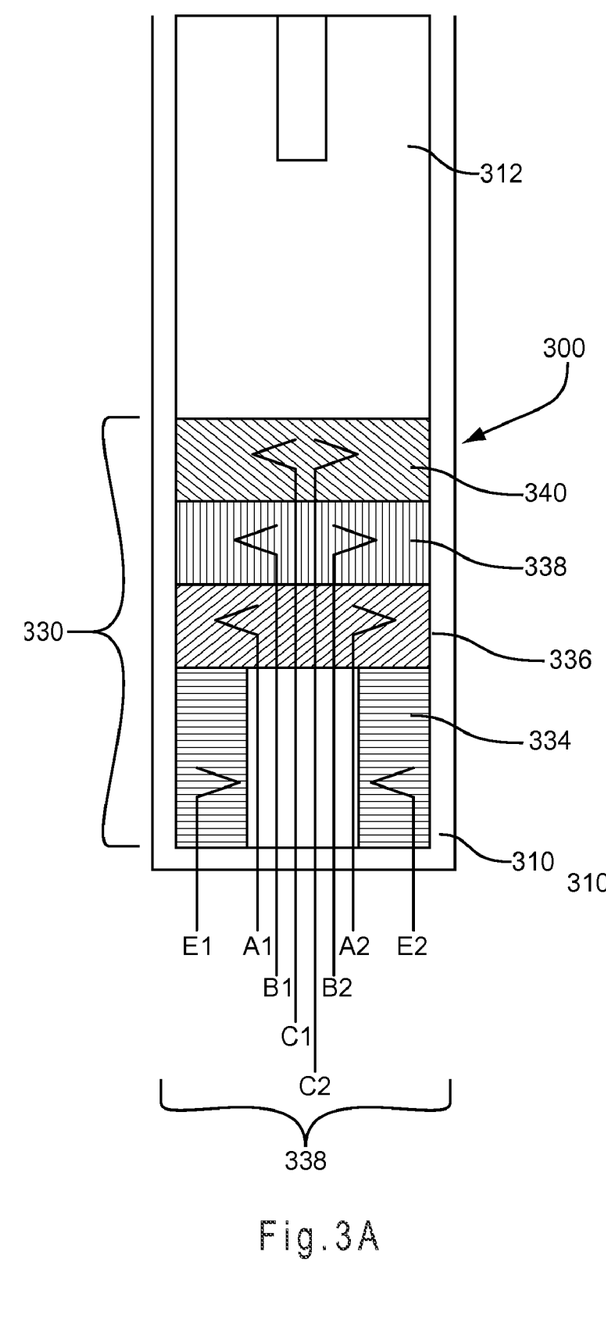
FIGS. 3A and 3B represent top and side views of another sensor strip including a substrate having a multi-layered encoding area, where an array of electrical contacts is in electrical communication with the encoding area.
Figure 3B:
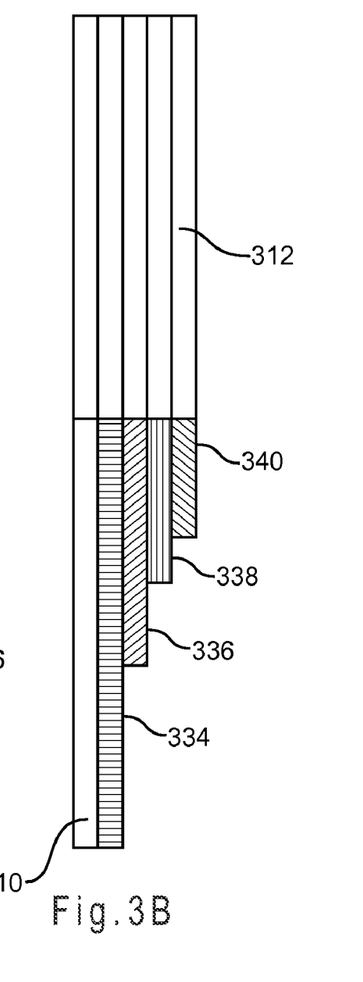

FIGS. 3A and 3B represent a sensor strip 300 including a substrate 310 and a cover 312 having a multi-layered encoding area 330, where an array of electrical contacts 338 (E1, A1, B1, C1, C2, B2, A2, and E2) is in electrical communication with the encoding area 330. The multi-layered encoding area 330 includes a first conductive layer 334, a second conductive layer 336, a third conductive layer 338, and a fourth conductive layer 340. The first conductive layer 334 may serve as the substrate 310. An insulator or an additional conductive layer may reside between one or more of the conductive layers 334, 336, 338, 340. The fourth conductive layer 340 may serve as the cover 312 of the sensor strip 300. While not shown in the figure, one or more of the conductive layers may be cut between the left and right contact areas to electrically isolate the first series of contacts from the second series of contacts as previously discussed.

One or more of the conductive layers may be removed from the area under a contact to provide different circuit patterns. For example, by removing the third and fourth conductive layers 338, 340 from beneath contact C1, electrical connectivity may be established between A1, A2, and C1. Thus, selectively removing one or more conductive layers from beneath one or more contacts provides different electrical connectivity between the contacts.

Figure 4A:
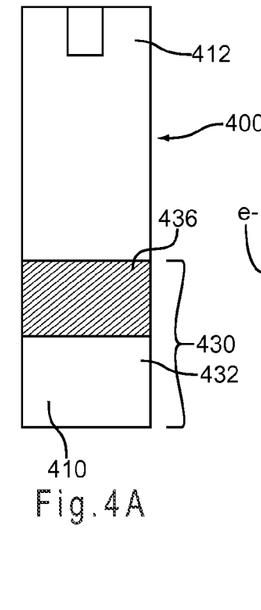
FIGS. 4A and 4B represent top and side views of a sensor strip including a substrate having a multi-layered encoding area, where light from a source is passed through the strip to a detector.
Figure 4B:
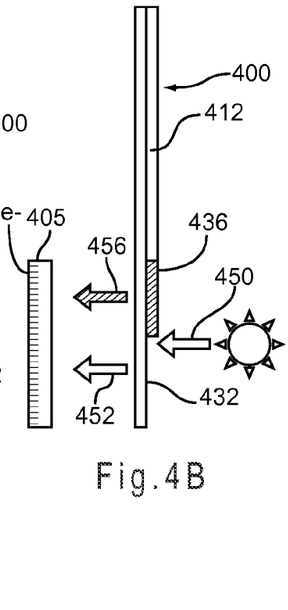

FIGS. 4A and 4B represent a sensor strip 400 including a substrate 410 and a cover 412 having a multi-layered encoding area 430, where light from a source is passed through the strip 400 to a detector 405. The multi-layered encoding area 430 includes a first transparent layer 432, which does not substantially alter the light, and at least one second transparent layer 436, which alters the light. As previously discussed, the alteration may be in the form of color, refractive index, transmittance, absorbance, and the like. The first transparent layer 432 may serve as the substrate 410, while the second transparent layer 436 may serve as the cover 412 of the sensor strip 400. Other layer configurations may be used.

In FIG. 4B, a light beam 450 passes through the first transparent layer 432 to provide the unaltered light beam 452 and through the second transparent layer 436 to provide a first altered light beam 456. The light beam may be generated in response to a test signal from a pattern read device, for example. The light beams 452, 456 are received by the detector 405. The detector may convert the received light beams into an analog or digital electrical signal representing the position, intensity, and the like of the altered and unaltered light beams. This electrical representation may be passed to a processor in the measurement device. The processor may convert the digital or analog representation into the calibration information.

Figure 4C:
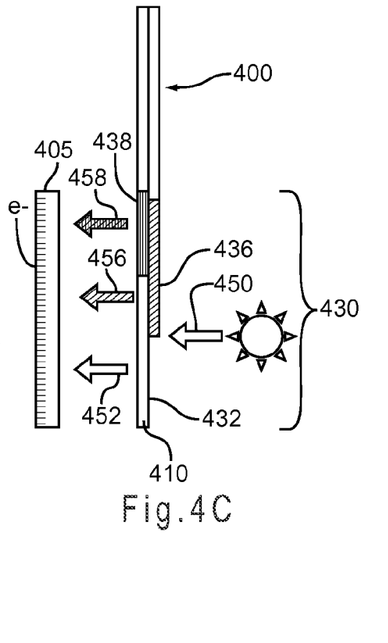
FIG. 4C represents a side view of a sensor strip having a multi-layered encoding area, where a portion of the substrate is formed from the second transparent layer and a third transparent layer is deposited on a portion of the second transparent layer.

FIG. 4C depicts the multi-layered encoding area 430 where a portion of the substrate 410 is formed from the first and a third transparent layer 432 and 438, respectively, and the second transparent layer 436 is disposed on a portion of the first and third transparent layers 432, 438. The second transparent layer 436 may serve as the cover 412 of the sensor strip 400.

As the light beam 450 passes through the encoding area 430, the beam passes through the first transparent layer 432 to provide the unaltered light beam 452, through the second transparent layer 436 to provide the first altered light beam 456, and through the second and third transparent layers 436, 438 to provide a second altered light beam 458. The detector may convert the received light beams into an analog or digital electrical signal representing the position, intensity, and the like of the first altered, second altered, and unaltered light beams.

In FIG. 4C, if a color change is the desired alteration of the light beam, for example, the first transparent layer 432 may be clear, the second transparent layer 436 may be yellow, and the third transparent layer 438 may be blue. When the light beam 450 passes through the strip 400 the detector 405 will detect the unaltered light beam 452 as clear, the first altered light beam 456 as yellow, and the second altered light beam 458 as green from the combined alteration of the second and third transparent layers 436, 438.

Table III, below, provides the possible color alterations of a light beam 450 from a strip having three transparent areas. For the sensor 400 of FIG. 4C the detector may detect three possible states of the light beam (clear, yellow, and green). While not shown in FIG. 4C light passing only through the first transparent layer 432 in addition to the third transparent layer 438 would be blue. Such a sensor strip construction may be provided by not disposing or removing a portion of the second transparent layer 436 from the third transparent layer 438.

TABLE III

| FIG. No. 4C | Transparent Layer 432 | Transparent Layer 436 | Transparent Layer 438 |
| --- | --- | --- | --- |
| Transparent Layer 432 | Clear (000) | Yellow (010) | Blue (001) |
| Transparent Layer 436 | Yellow (010) | Yellow (010) | Green (100) |
| Transparent Layer 438 | Blue (001) | Yellow (010) | Blue (001) |

The detector 405 and associated electronics may then convert the received color composition and/or pattern into the calibration information. For example, each color may be translated into a numerical value as shown in Table III. The color composition and/or pattern may be converted into an established coding method, such as the Hex Triplet method that uses three bytes of a hexadecimal number. For example, blue may be represented as 0000FF, green as 008000, yellow as FFFF00, and clear (unaltered) as FFFFFF. One or more of the numerical or other values alone or in combination may provide the desired calibration information, such as a specific lot number of the sensor strip.

As previously discussed regarding electrical encoding areas, multiple portions of the material forming the second and/or third transparent layers 436, 438 may be removed in any shape to provide differences in the light beams received by the detector 405. Thus, in addition to the alteration of the light beam 450 caused by one or more transparent layers, the shape and/or pattern of the light beams received by the detector may be used to provide calibration information to the system.

Figure 4D:
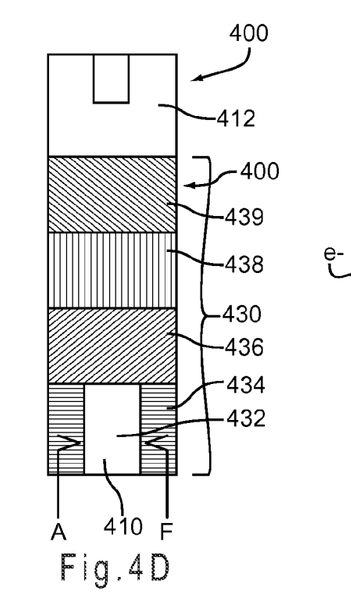
FIGS. 4D and 4E represent top and side views of a sensor strip having a multi-layered encoding area, where the substrate is formed from the first transparent layer, the second transparent layer is deposited on a portion of the first transparent layer, the third transparent layer is deposited on a portion of the second transparent layer, and a fourth transparent layer is deposited on a portion of the third transparent layer.

FIG. 4D represents the multi-layered encoding area 430 where the substrate 410 is formed from the first transparent layer 432, the second transparent layer 436 is disposed on a portion of the first transparent layer 432, the third transparent layer 438 is disposed on a portion of the second transparent layer 436, and a fourth transparent layer 439 is disposed on a portion of the third transparent layer 438. In addition to the transparent layers 432, 436, 438, 439, the multi-layered encoding area 430 also includes one or more electrically conductive layers 434. The fourth transparent layer 439 may serve as the cover 412 of the sensor strip 400.

Figure 4E:
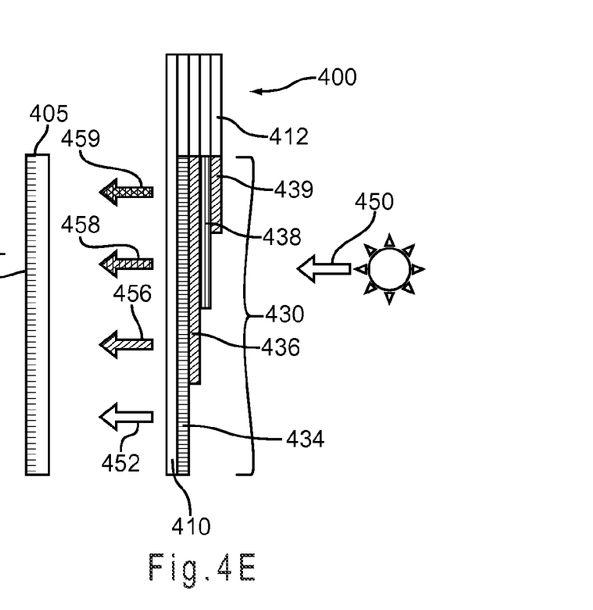

In FIG. 4E, in addition to the unaltered light beam 452, the first altered light beam 456, and the second altered light beam 458, the fourth transparent layer 439 provides for a third altered light beam 459. As previously discussed, one or more portions of the material forming the transparent layers may be removed in any shape to provide differences in the light beams received by the detector 405. The shape and/or pattern of the light beams received by the detector also may be used to provide calibration information to the system. Coding information also may be derived from one or more of the conductive layers 434 as previously discussed. In this manner, electrical and optical layers may be used in the encoding area 430 to provide calibration information to the measurement device.

Figure 5:
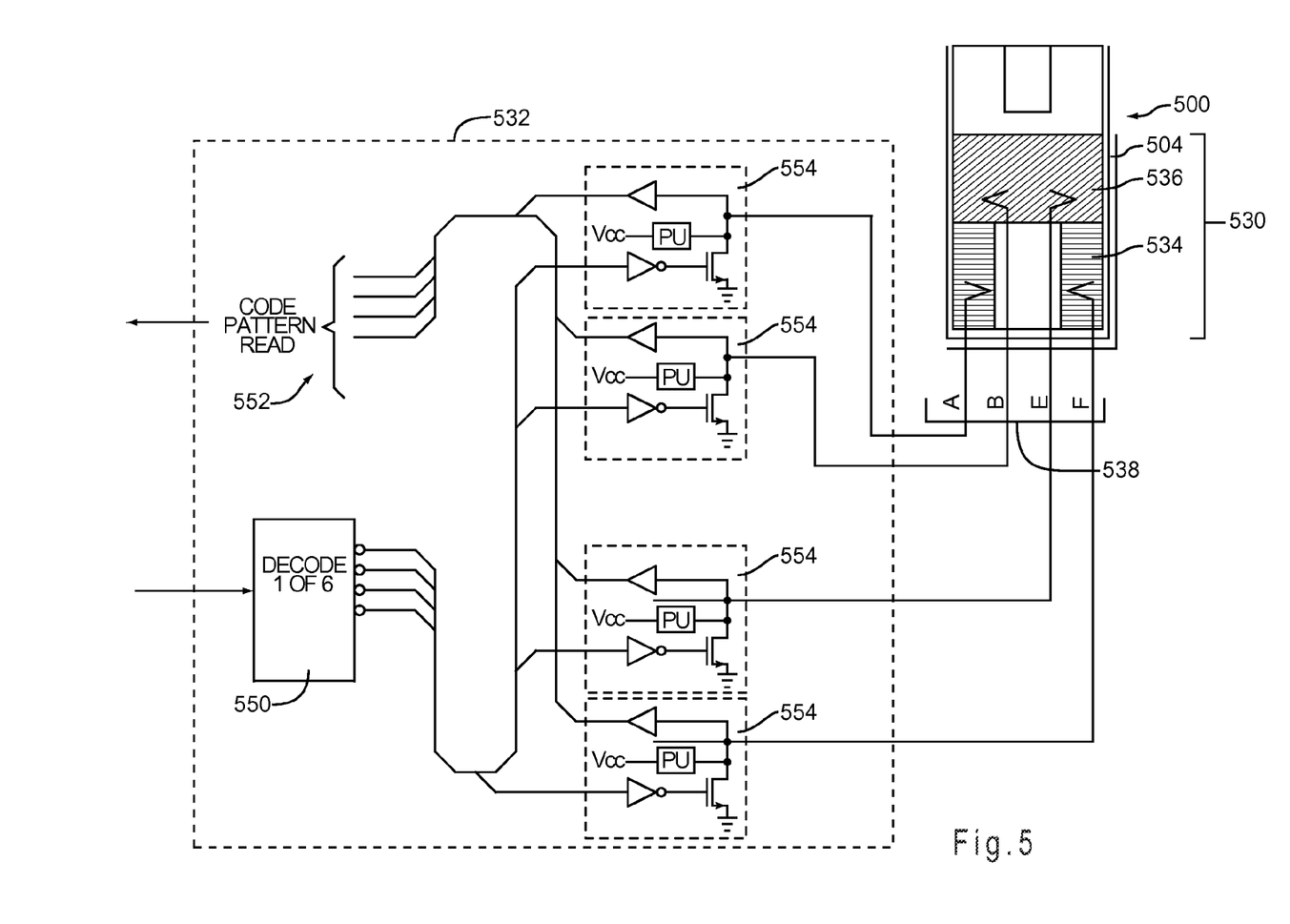
FIG. 5 represents a pattern read device.

FIG. 5 depicts a pattern read device 532 for sensing the circuit patterns of an encoding area 530 on a sensor strip 500. The encoding area 530 has a first layer 534 and a second layer 536. While the sensor strip 500 includes two isolated contact areas in electrical communication with electrical contacts A and F, respectively, sensors trips with fewer or additional isolated contact areas may be used.

The pattern read device 532 has a decoder 550 and a code reader 552, each connected to a plurality of test circuits 554. While four test circuits are shown, fewer or additional of the test circuits 554 may be used. The decoder 550 may be a digital decoder or like device. The decoder 550 may be a select one of 'n' digital decoder. The decoder 550 may be a select one of 'n' digital decoder, where n=4. Other digital decoders may be used. The code reader 552 may be a digital input port or like device. Each test circuit 554 is connected to a separate electrical contact A, B, E, or F in an array of electrical contacts 538. The electrical contacts A-F may have electrical communication with the first layer 534 and the second layer 536 of the encoding area 530. While a particular layer arrangement is shown, others may be used. While a particular configuration is shown for the pattern read device, other configurations may be used including those with additional components. Other pattern read devices may be used.

In use, a processor sends a control signal to the decoder 550 in the pattern read device 532. The processor also activates a pull-up voltage in each of the test circuits 554. The pull-up voltage may cause each test circuit 554 to apply a test signal or current to the electrical contacts A-F in the array 538. The test signals may be limited to a current of less than about 50 µA. The test signals may be current limited in the range of about 1 µA through about 48 µA, about 2 µA through about 15 µA, about 2 µA through about 10 µA, or about 4 µA through about 8 µA. Other currents may be used. The processor also activates the code reader 552 to sense the test signals applied to each electrical contact in the array 538.

The pattern read device 532 selectively applies the test signals to determine the circuit patterns of layers 534 and 536 of the encoding area 530. The test circuits 554 apply the test signals to the electrical contacts A-F of array 538. The code reader 552 senses the test signals. To sense the connectivity patterns, the pattern read device 532 individually drives one or more electrical contacts in the array 538 to ground while applying pull-up voltage test signals to the other electrical contacts in the array 538. The decoder 550 applies an operating signal to one or more of test circuits 554 in response to the control signal. The operating signal drives the respective test circuit and corresponding electrical contact to ground.

The multiple layers of the encoding area 530 provide varied electrical connectivity between the contacts A-F of the array 538. When a particular electrical contact on a circuit is driven to ground, the test signals of the other electrical contacts on the circuit are reduced or driven to ground. The code reader 552 uses the reduced or grounded test signals to identify the electrical contacts associated with the particular electrical contact that was driven to ground. The electrical contacts associated with the grounded electrical contact may be used to identify the circuit pattern. The code reader 552 generates a pattern signal that identifies the circuit patterns on the encoding label 530. The pattern signal may be a digital representation of the circuit patterns. The processor receives the pattern signal from the code reader 552. The pattern signal may include calibration information. The processor may convert the pattern signal into calibration information or use the pattern signal to locate calibration information in a storage medium. The processor uses calibration information to calibrate one or more correlation equations used to determine the analyte concentration in the biological fluid.

The pattern read device may apply the test signals in one or more steps or iterations. Different contacts are driven to ground in each step. After one or more steps, the pattern read device may determine the unique set of electrical contacts corresponding to a particular connectivity by determining which contacts have reduced or grounded test signals in response to being driven to ground. Thus, the pattern read device can determine the unique set of contacts in the array 538 that are associated with the specific connectivity between the first and second layers 534, 536 of the encoding area 530. The unique sets of the electrical contacts identify the connectivity between the first and second layers 534, 536. The connectivity may be used to provide calibration information for the optical or electrochemical analysis of an analyte in a biological fluid.

Figure 6A:
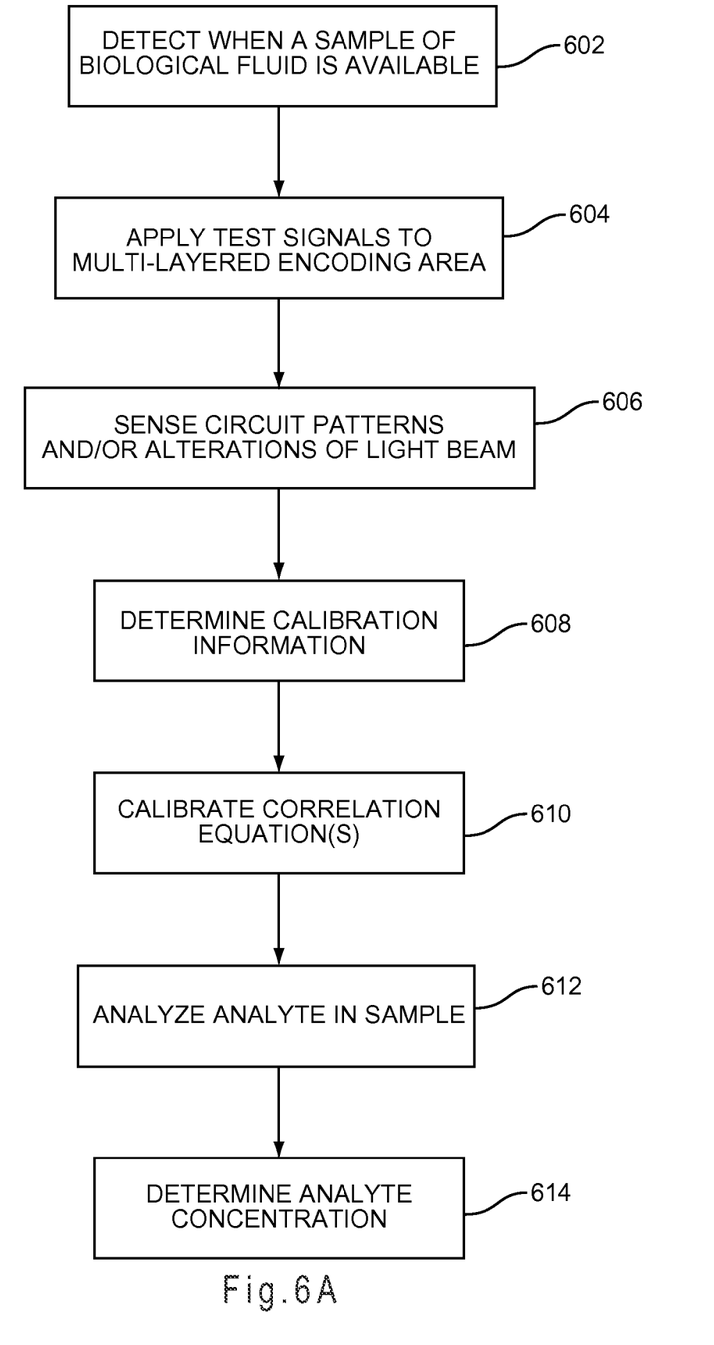
FIGS. 6A and 6B represent methods for calibrating an analysis.
Figure 6B:
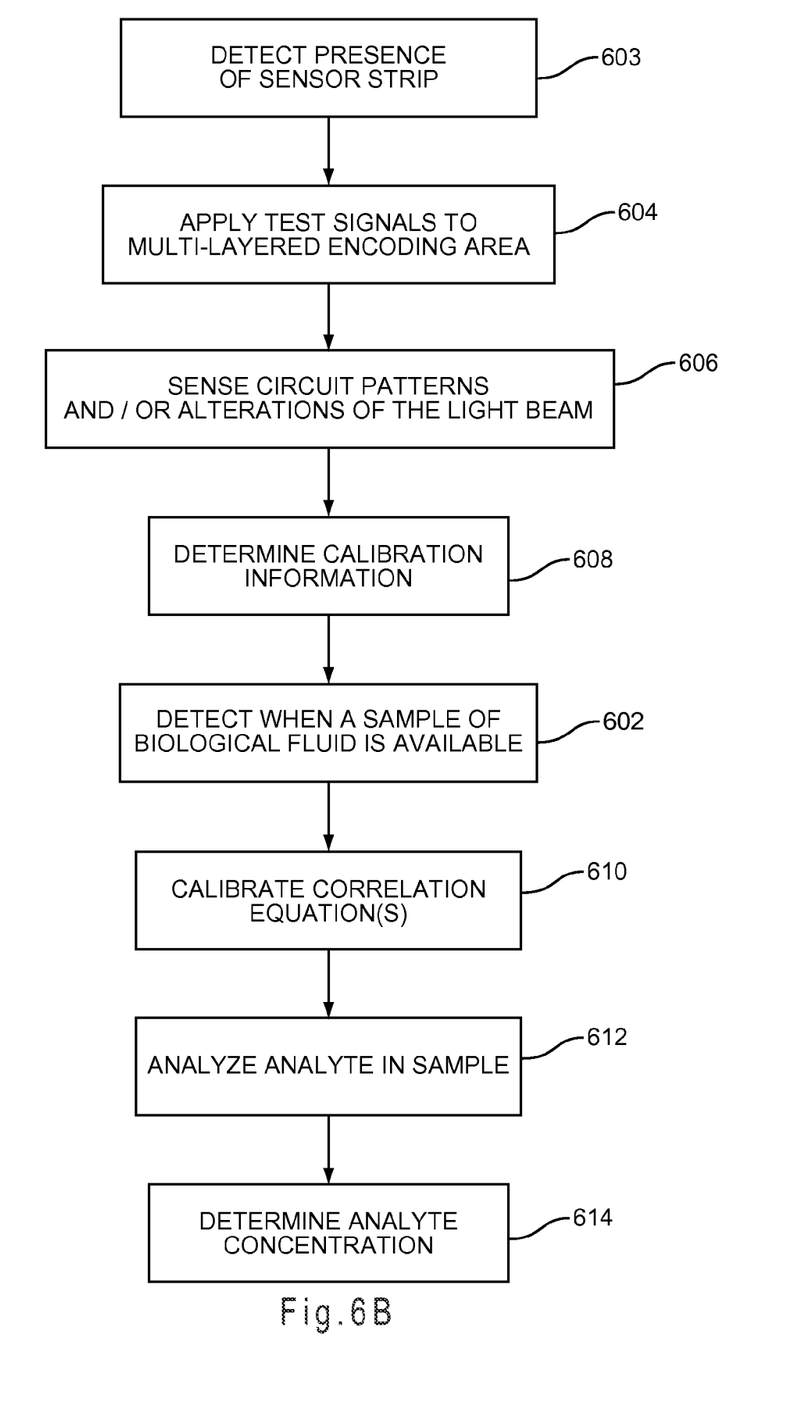

FIGS. 6A and 6B represent methods for calibrating an electrical or optical analysis of an analyte in a sample of biological fluid. In 602, a sample of a biological fluid is detected when available for analysis. In 604, test signals that may be generated optically or electrically are applied to a multi-layered encoding area. In 606, electrical connectivity and/or alterations of a light beam from the encoding area are sensed. In 608, calibration information is determined in response to the connectivity and/or alterations. In 610, one or more correlation equations are calibrated in response to the calibration information. In 612, the analyte in the sample is analyzed. In 614, the analyte concentration of the biological fluid is determined using one or more calibrated correlation equations.

In 602, a biosensor detects when a sample of biological fluid is available for analysis. The biosensor may sense when a sensor strip is placed in a measuring device. The biosensor may sense (mechanically, electrically, or the like) when electrical contacts in the measuring device connect with electrical conductors in the sensor strip. The biosensor may apply one or more signals to the working, counter, and/or other electrodes to detect when a sample connects with the electrodes. The biosensor may use other methods and devices to detect when a sample is available for analysis.

In 604, the biosensor applies test signals from a measurement device to an encoding area on a sensor strip, sensor strip package, or the like. The test signals may be optical or electrical and may be applied in one or more steps or iterations. In 606, the biosensor senses the circuit patterns and/or alterations of the light beam resulting from the encoding area.

In 608, the biosensor determines the calibration information in response to the circuit patterns and/or light beam alterations. The calibration information may be any information used to adjust correlation equations for electrochemical and/or optical analyses. Calibration information may be identification information indicating the type of sensor strip, the analyte(s) or biological fluid associated with the sensor strip, the manufacturing lot of the sensor strip, or the like. Calibration information may provide an addition or subtraction to the slope and/or intercept of a correlation equation. Calibration information may include or direct the use of a slope and intercept for a correlation equation. The calibration information may reference parameters and adjustments stored in a memory device in the biosensor. A processor may select stored reference parameters and adjustments in response to a pattern or other signal indicating the circuit patterns and/or light beam alterations from the encoding label.

In 610, the biosensor calibrates one or more correlation equations in response to the calibration information. Calibrate includes adjusting or modifying the concentration value or other result of a correlation equation. Calibrate may include selecting one or more correlation equations in response to identification information indicating the type of sensor strip, the analyte(s) or biological fluid associated with the sensor strip, the manufacturing lot of the sensor strip, the expiration date of the sensor strip, or the like. Calibrate may include modifying one or more correlation equations with an addition or subtraction to the slope and/or intercept of the correlation equation. Calibrate may include providing one or more of the correlation equations.

Correlation equations may be used to determine the presence and/or the analyte concentration during analyzes. Correlation equations are mathematical representations of the relationship between analyte concentrations and output signals such as light, current, or potential. The correlation equations may be linear, near linear, or curvilinear and may be described by a second order polynomial. From a correlation equation, an analyte concentration may be calculated for a particular output signal.

The biosensor may have one or more correlation equations stored in a memory for use during the optical or electrochemical analysis. Different correlation equations may be needed, especially when different sensor strips are used or operating parameters such as the sample temperature change. Correlation equations may be implemented to manipulate the output signal for determination of the analyte concentration. Correlation equations also may be implemented as a program number assignment (PNA) table of the slope and intercept for the correlation equations, another look-up table, or the like for comparison with the output signals to determine the analyte concentration.

In 612, the biosensor analyzes the analyte in the sample using an electrochemical analysis, an optical analysis, a combination thereof, or the like. During electrochemical analyses, an excitation signal is applied to the sample of the biological fluid. The excitation signal may be a potential or current and may be constant, variable, or a combination thereof. The excitation signal may be applied as a single pulse or in multiple pulses, sequences, or cycles. Various electrochemical processes may be used such as amperometry, coulometry, voltammetry, gated amperometry, gated voltammetry, and the like.

An optical analysis generally measures the amount of light absorbed or generated by the reaction of a chemical indicator with the analyte. An enzyme may be included with the chemical indicator to enhance the reaction kinetics. The light from an optical system may be converted into an electrical signal such as current or potential by a detector.

In light-absorption optical analyses, the chemical indicator produces a reaction product that absorbs light. An incident excitation beam from a light source is directed toward the sample. The incident beam may be reflected back from or transmitted through the sample to a detector. The detector collects and measures the attenuated incident beam. The amount of light attenuated by the reaction product is an indication of the analyte concentration in the sample.

In light-generated optical analyses, the chemical indicator produces a reaction product that fluoresces or emits light in response to the analyte during the redox reaction. A detector collects and measures the generated light. The amount of light produced by the chemical indicator is an indication of the analyte concentration in the sample.

In 614, the biosensor determines the presence and/or the concentration of the analyte in the sample. The data from the analyte analysis may be subjected to one or more data treatments, including the determination of decay rates, K constants, slopes, intercepts, and/or sample temperature. The biosensor may use one or more of the calibrated correlation equations to determine the analyte concentration of the sample. The biosensor may use the calibrated analyte value or other result to determine the analyte concentration of the sample. The calibrated analyte value or other result may increase the accuracy and/or precision of the analysis. Accuracy may be expressed in terms of bias of the sensor system's analyte reading in comparison to a reference analyte reading, with larger bias values representing less accuracy, while precision may be expressed in terms of the spread or variance among multiple measurements.

FIG. 6B represents another method for calibrating an analysis of an analyte in a biological fluid. In 603, a measuring device detects the presence of a sensor strip in a biosensor. The measuring device may sense (mechanically, electrically, or the like) when electrical contacts in the measuring device connect with electrical conductors and/or the encoding area on the sensor strip. The measuring device may apply one or more signals to the working, counter, and/or other electrodes to detect when a sensor strip is present. The measuring device may apply one or more signals to the encoding area to detect when a sensor strip is present. The measuring device may use other methods and devices to detect when a sensor strip is present.

Figure 7:
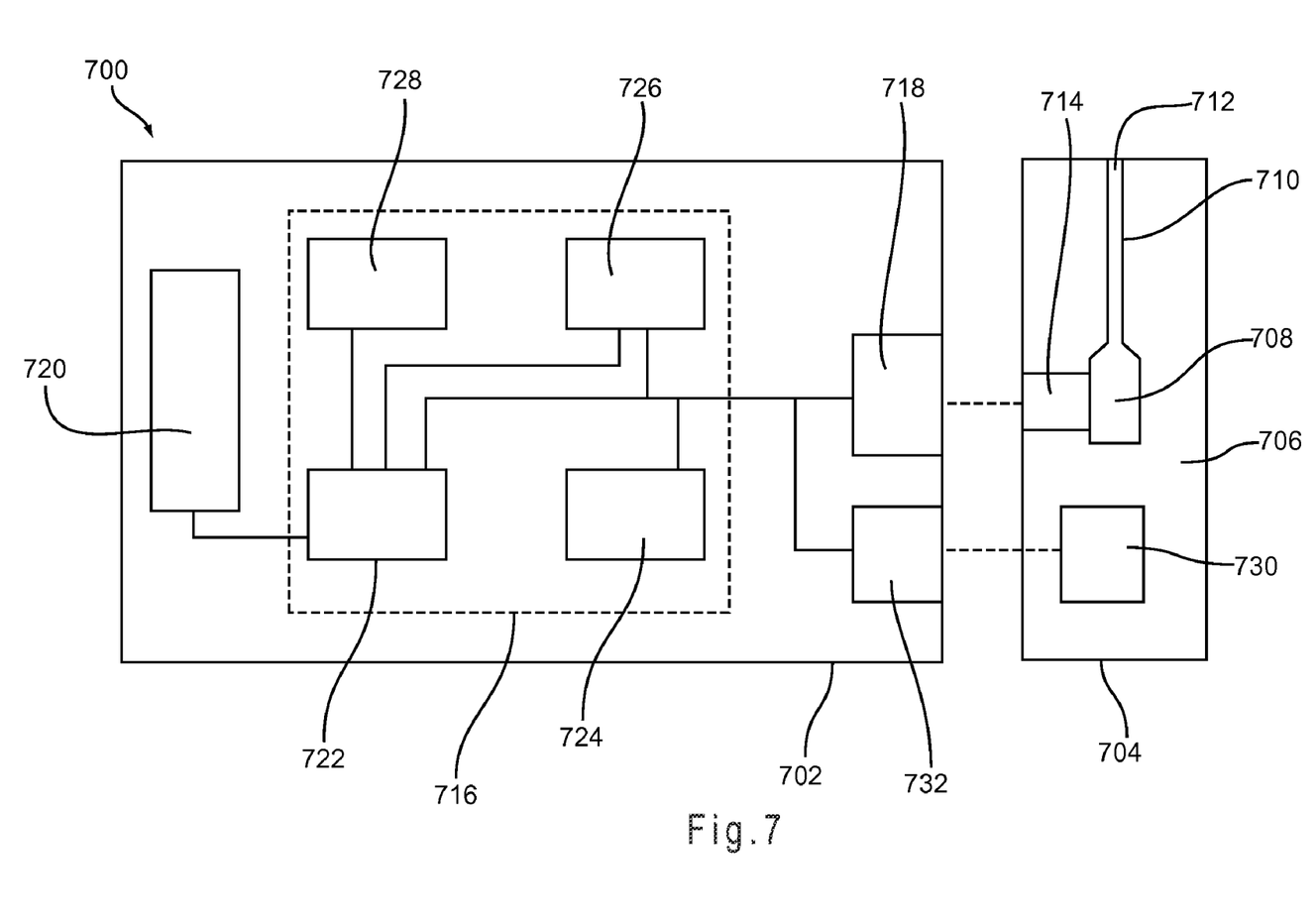
FIG. 7 is a schematic representation of a biosensor system that determines the presence and/or the concentration of an analyte in a sample.

FIG. 7 depicts a schematic representation of a biosensor system 700. The biosensor system 700 includes a measurement device 702 and a sensor strip 704. Measurement devices may apply an electrical and/or optical signal and measure one or more resulting electrical or optical signals during an analysis. The measurement device may have the processing capability to determine the presence and/or concentration of one or more analytes in the sample.

The sensor strip 704 has a base 706 that forms a sample reservoir 708 and a channel 710 with an opening 712. The reservoir 708 and the channel 710 may be covered by a lid with a vent. The reservoir 708 defines a partially-enclosed volume. The sensor strip 704 may have a sample interface 714. In an electrochemical system, the sample interface 714 may have conductors connected to at least two electrodes, such as a working electrode and a counter electrode. The electrodes may be disposed on a surface of the base 706 that forms the reservoir 708. The sensor strip 704 and the sample interface 714 may have other electrodes, conductors, and/or configurations.

The sensor strip 704 may have a multi-layered encoding area 730 on the base 706, as previously discussed. The encoding area 730 may be a separate label affixed to the sensor strip 704 or elsewhere on the biosensor system 700, or the encoding area 730 may be formed on the base 706. The encoding area 730 may be formed using the same materials and similar techniques as used to create conductive measurement traces to reservoir 708, the conductors or electrodes on the sample interface 714, other components of the sensor strip 704, or the like.

The encoding area 730 may be located on the top, bottom, sides, or any other location on the sensor strip 704. The encoding area 730 may be on separate strips. For example, the encoding area 730 may be on a calibration strip for use with a set of measuring strips. The calibration strip may be another strip or may be part of or attached to a package containing the set of measuring strips. In addition, the calibration strip and the measuring strips each may have an encoding area. For example, the calibration strip may have a first encoding area that provides more general calibration information while each measuring strip may have a second encoding area that provides more specific calibration information. Other encoding areas may be used.

The measurement device 702 includes electrical circuitry 716 connected to a sensor interface 718, a display 720, and a pattern read device 732. The sensor interface 118 and the pattern read device 732 may be the same component. The electrical circuitry 716 may include a processor 722 connected to a signal generator 724, an optional temperature sensor 726, and a storage medium 728. Electrical circuitry 716 may have other configurations including those with additional components. The storage medium 728 may be a magnetic, optical, or semiconductor memory, another computer readable storage device, or the like. The storage medium 728 may be a fixed memory device or a removable memory device such as a memory card.

Each circuit on the encoding label 730 may have one or more contact areas that are in electrical communication with the pattern read device 732. When each circuit has at least two contact areas, the detection of faulty contacts, open circuit conditions, and other errors from additional or missing material may be improved. The detection of these errors also may be improved when the encoding label 730 has two circuits that include all of the contact areas. The same number of circuits may be used on different strips to improve further the detection of these errors. When an error occurs, the measurement device 702 may notify the user and may reject and/or eject the sensor strip 704. Error checking may include determining whether a count of the circuit patterns matches the number of circuits on the encoding label 730. If the measurement device 702 cannot account for all the contact areas and all the circuit patterns on the encoding label 730, the measurement device 102 also may notify the user and may reject and/or eject the sensor strip 704.

The processor 722 provides a control signal to the pattern read device 732. The control signal may be an electrical signal such as potential, current, or the like. In optical systems, the control signal operates a first light source and a first detector in the pattern read device 732. In electrical systems, the control signal may operate electrical contacts in the pattern read device 732 that are in electrical communication with contact areas on the encoding area 730. Electrical communication includes the transfer of signals between electrical contacts in the pattern read device 732 and contact areas in the encoding area 730. Electrical communication may be implemented wirelessly or through physical contact.

The pattern read device 732 senses the optical or circuit patterns of the encoding area 730, and provides a pattern signal to the processor 722. The pattern read device 732 and/or processor 722 may combine the code signals to form a check signal. "Combine" includes summing, comparing, and the like operations on the code signals. The check signal may be used to identify errors, adjust the code signals for variability in the insertion rate of the sensor strip into the measurement device, or the like. The code and check signals may be digital signals or the like. "Digital signals" includes electrical signals that discretely switch between the presence and absence of current, switch between high and low potentials, or the like. "Discretely switch" includes substantially instantaneous transitions from one current, potential, or signal level to another.

Digital signals may be transmitted as binary or other code. The processor 722 converts the code signals into the coding information for use with the sensor strip 704. In response to the code and check signals, the processor 722 may calibrate one or more of the correlation equations, identify the sensor strip, make a determination regarding the analyte analysis, a combination thereof, or the like.

The signal generator 724 provides an electrical input signal to the sensor interface 718 in response to the processor 722. In optical systems, the electrical input signal operates a light source and a detector in the sensor interface 718. In electrochemical systems, the electrical input signal is transmitted by the sensor interface 718 to the sample interface 714 to apply the electrical input signal to the reservoir 708 and thus, to the sample of the biological fluid.

The sensor interface 718 is in electrical and/or optical communication with the sample interface 714. Electrical communication includes the transfer of input and/or output signals between contacts in the sensor interface 718 and conductors in the sample interface 714. Electrical communication may be implemented wirelessly or through physical contact. The sensor interface 718 transmits the electrical input signal from the signal generator 724 through the contacts to the connectors in the sample interface 714. The sensor interface 718 also transmits the output signal from the sample through the contacts to the processor 722 and/or the signal generator 724. Optical communication includes the transfer of light between an optical portal in the sample interface 702 and a detector in the sensor interface 708. Optical communication also includes the transfer of light between an optical portal in the sample interface 702 and a light source in the sensor interface 708.

Similarly, the pattern read device 732 is in electrical or optical communication with the encoding area 730. Electrical communication includes the transfer of signals between the pattern read device 732 and the encoding area 730. Electrical communication may be implemented wirelessly or through physical contact. Optical communication includes the transfer of light from a light source in the pattern read device 732 to the encoding area 730. Optical communication also includes the transfer of light from the encoding area 730 to a detector in the pattern read device 732.

The display 720 may be analog or digital. The display 720 may be a LCD, LED, or vacuum fluorescent display adapted to displaying a numerical reading.

The biosensor system may be operated with sensor strips designed for a single analysis of the analyte concentration in the biological fluid. The biosensor system also allows a larger number of different calibration information to be used. The calibration may be implemented digitally, thus making the analyte analysis more tolerant of resistance differences between sensor strips from the manufacture of the encoding label and other resistance variations. A biosensor also may have more robust error detection of failures because all electrical contacts in the pattern read device must electrically or optically communicate with the corresponding contact areas of the circuits on the encoding label for accurate and precise sensing of the circuit patterns. The biosensor may notify the user and may reject and/or eject the sensor strip when all the electrical contacts in the pattern read device do not electrically or optically communicate with the corresponding contact areas of the encoding area. The error detection may reduce or eliminate misreads of the circuit patterns and the selection of incorrect calibration information, thus avoiding biased or incorrect analysis of the analyte. The detection and reading of valid calibration patterns may be used to indicate the proper insertion of a sensor into the measurement device.

While various embodiments of the invention have been described, it will be apparent to those of ordinary skill in the art that other embodiments and implementations are possible within the scope of the invention.

What is claimed is:

1. A biosensor for determining a characteristic of a biological sample, comprising:
   an analysis device having a processor connected to a pattern read device;
   a sensor element having a multi-layered encoding area with at least a first layer and a second layer, the first layer and the second layer defining at least one pattern that provides encoding information for the analysis device, at least a portion of the second layer being disposed on at least a portion of the first layer, the portion of the second layer being non-coplanar with the portion of the first layer, the portion of the second layer covering the portion of the first layer relative to the pattern read device;
   where the analysis device and sensor element implement an sample analysis, where the sample analysis has at least one analysis equation;
   where the pattern read device directly reads the first layer and the second layer to determine the at least one pattern;
   where the processor determines encoded information responsive to the at least one pattern;
   where the processor executes the at least one analysis equation according to the encoded information; and
   where the processor determines a characteristic of a biological sample according to the at least one analysis equation and the encoded information.

2. The biosensor of claim 1, the multi-layered encoding area further comprising a third layer.

3. The bio sensor of claim 1, where
   the pattern read device employs one or more contacts that sense the multi-layered encoding area through electrical connectivity, each layer includes two or more contact areas, and each contact area is in electrical communication with the one or more contacts.

4. The biosensor of claim 1, where the pattern read device selectively applies test signals to the multi-layered encoding area.

5. The biosensor of claim 4, where the pattern read device senses the multi-layered encoding area through electrical connectivity and the pattern read device applies test signals to the multi-layered encoding area, and where the pattern read device drives at least one test signal to ground.

6. The biosensor of claim 1, comprising at least one circuit having electrical connectivity between the first and second layers, where the pattern read device senses the multi-layered encoding area through electrical connectivity.

7. The biosensor of claim 1, where the pattern read device senses the multi-layered encoding area through an alteration of a light beam applied to the multi-layered encoding area and the alteration is selected from the group consisting of color, refractive index, fluorescence, absorption, transmission, reflection, refraction, scattering, shape, and combinations thereof.

8. A biosensor for determining a characteristic of a biological sample, comprising:
   an analysis device having a processor connected to a pattern read device, where the pattern read device has an array of electrical contacts;
   a sensor element having a multi-layered encoding area with at least a first layer and a second layer, the first layer and the second layer defining at least one pattern that provides encoding information for the analysis device, at least a portion of the second layer being disposed on at least a portion of the first layer, the portion of the second layer being non-coplanar with the portion of the first layer, where the encoding area has at least two electrical connectivities, where at least one connectivity has at least one contact area on the first layer and at least one contact area on the second layer, where the contact areas are in direct electrical communication with the electrical contacts, the portion of the second layer keeping the portion of the first layer from being in contact with the electrical contacts by covering the portion of the first layer relative to the electrical contacts;

where the analysis device and sensor element implement a sample analysis, where the sample analysis has at least one analysis equation;

where the electrical contacts selectively apply test signals to the contact areas on the encoding area;

where the pattern read device senses the at least two electrical connectivities on the encoding area;

where the processor determines encoded information responsive to the at least two electrical connectivities;

where the processor executes the at least one analysis equation according to the encoded information; and where the processor determines a characteristic of a biological sample according to the at least one analysis equation and the encoded information.

9. The biosensor of claim 8, where each connectivity has at least two contact areas, and where the contact areas are in electrical communication with the electrical contacts.

10. The biosensor of claim 8, comprising at least one connectivity having an electrical connection between the first and second layers of the encoding area.

11. The biosensor of claim 8, where the pattern read device generates a pattern signal responsive to the connectivities.

12. The biosensor of claim 8, where the contact areas on the encoding area are arranged in at least two rows and in at least two columns and each row resides on a different layer.

13. A method for determining a characteristic of a biological sample, comprising:

sensing, with a pattern read device of an analysis device, a multi-layered encoding area, the multi-layered encoding area having at least a first layer and a second layer, at least a portion of the second layer being disposed on at least a portion of the first layer, the first layer and the second layer defining at least one pattern that provides encoding information for the analysis device, the portion of the second layer being non-coplanar with the portion of the first layer, the portion of the second layer covering the portion of the first layer relative to the pattern read device, the pattern read device directly reading the first layer and the second layer to determine the at least one pattern;

determining, with a processor of the analysis device, the encoding information in response to the at least one pattern;

executing, with the processor of the analysis device, at least one analysis equation on the analysis device according to the encoded information; and determining, with the processor of the analysis device, a characteristic of a biological sample according to the at least one analysis equation and the encoded information.

14. The method of claim 13, further comprising:
applying test signals to the encoding area; and
driving at least one test signal to ground, when the pattern read device senses the multi-layered encoding area through electrical connectivity.

15. The method of claim 14, further comprising applying at least one other test signal at a pull-up voltage.

16. The method of claim 13, further comprising:
driving a first test signal to ground during a first step; and
driving a second test signal to ground during a second step, when the pattern read device senses the multi-layered encoding area through electrical connectivity.

17. The method of claim 16, further comprising driving a third test signal to ground during a third step.

18. The method of claim 13, further comprising generating a pattern signal responsive to the patterns.

19. The method of claim 13, where the pattern is the electrical connectivity and each connectivity has at least two contact areas.

20. The method of claim 13, where the pattern is the alteration of the light beam and the alteration is selected from the group consisting of color, refractive index, fluorescence, absorption, transmission, reflection, refraction, scattering, shape, and combinations thereof.

21. The biosensor of claim 1, wherein the at least one analysis equation includes at least one correlation equation, the encoded information includes calibration information, the processor calibrates the at least one correlation equation responsive to the calibration information, and the processor determines an analyte concentration responsive to the at least one correlation equation calibrated with the calibration information.

22. The biosensor of claim 8, wherein the at least one analysis equation includes at least one correlation equation, the encoded information includes calibration information, the processor calibrates the at least one correlation equation responsive to the calibration information, and the processor determines an analyte concentration responsive to the at least one correlation equation calibrated with the calibration information.

23. The method of claim 13, wherein the at least one analysis equation includes at least one correlation equation, the encoded information includes calibration information, executing the at least one analysis equation includes calibrating at least one correlation equation according to the calibration information, and determining a characteristic of a biological sample includes determining an analyte concentration responsive to the at least one correlation equation calibrated with the calibration information.

24. The bio sensor of claim 1, wherein multi-layered encoding area includes an insulator that substantially electrically isolates the first layer from the second layer.

25. The biosensor of claim 8, wherein the multi-layered encoding area includes an insulator that substantially electrically isolates the first layer from the second layer.

26. The method of claim 13, wherein the multi-layered encoding area includes an insulator that substantially electrically isolates the first layer from the second layer.

* * * * *